US011478655B2

(12) United States Patent
Beattie, Jr. et al.

(10) Patent No.: US 11,478,655 B2
(45) Date of Patent: Oct. 25, 2022

(54) SMART AUTOMATED EXTERNAL DEFIBRILLATOR

(71) Applicant: AT&T Intellectual Property I, L.P., Atlanta, GA (US)

(72) Inventors: James Gordon Beattie, Jr., Bergenfield, NJ (US); Haywood S. Peitzer, Randolph, NJ (US)

(73) Assignee: AT&T Intellectual Property I, L.P., Atlanta, GA (US)

( * ) Notice: Subject to any disclaimer, the term of this patent is extended or adjusted under 35 U.S.C. 154(b) by 13 days.

(21) Appl. No.: 16/456,579

(22) Filed: Jun. 28, 2019

(65) Prior Publication Data

US 2020/0406046 A1 Dec. 31, 2020

(51) Int. Cl.
*A61N 1/04* (2006.01)
*A61N 1/39* (2006.01)
*A61B 5/318* (2021.01)

(52) U.S. Cl.
CPC ......... *A61N 1/3925* (2013.01); *A61N 1/3904* (2017.08); *A61N 1/3993* (2013.01); *A61B 5/318* (2021.01); *A61B 2562/0219* (2013.01); *A61N 1/046* (2013.01); *A61N 1/3975* (2013.01); *A61N 1/3987* (2013.01)

(58) Field of Classification Search
CPC ............................. A61N 1/3904; A61N 1/3993
See application file for complete search history.

(56) References Cited

U.S. PATENT DOCUMENTS

| 6,141,584 | A | * | 10/2000 | Rockwell | A61N 1/3904 |
| | | | | | 607/5 |
| 9,757,580 | B2 | | 9/2017 | Park et al. | |
| 2011/0060378 | A1 | * | 3/2011 | Tuysserkani | A61B 5/0022 |
| | | | | | 607/5 |
| 2015/0024738 | A1 | * | 1/2015 | Anderson | H04W 36/0094 |
| | | | | | 455/432.1 |
| 2016/0350553 | A1 | * | 12/2016 | Alameh | G06F 21/6245 |
| 2017/0003356 | A1 | * | 1/2017 | Kaib | G01R 31/389 |
| 2018/0280709 | A1 | * | 10/2018 | Taylor | A61N 1/3993 |
| 2019/0200168 | A1 | * | 6/2019 | Stapleford | H04W 4/029 |

OTHER PUBLICATIONS

Swedberg, Claire, "IoT Network Puts Defibrillator Management in Hands of Suppliers," RFID Journal, Nov. 26, 2018, https://www.rfidjournal.com/articles/view?17978.

(Continued)

*Primary Examiner* — Brian T Gedeon
*Assistant Examiner* — Joshua Andrew Schum-Houck
(74) *Attorney, Agent, or Firm* — Hartman & Citrin LLC

(57) ABSTRACT

Concepts and technologies disclosed herein are directed to a smart automated external defibrillator ("AED"). According to one aspect of the concepts and technologies disclosed herein, the AED can present a menu that includes a plurality of modes. The plurality of modes can include a first responder mode, an Internet of Things ("IoT") mode, and a general use mode. The AED can receive, via an input component, a selection, from the menu, of a mode from the plurality of modes. In response to the selection, the AED can configure a network connectivity component in accordance with a setting specified in the mode.

16 Claims, 9 Drawing Sheets

(56) References Cited

OTHER PUBLICATIONS

"Lead the way to save a life, Philips Heartstart OnSite defibrillator," Philips, May 2019, 2019 Koninklijke Philips N.V., www.philips.com/OnSite.

"Connected, Philips Heartstart connectivity and data management for ALS professionals," Philips, Jan. 2008, 2008 Koninklijke Philips Electronics N.V., www.philips.com/healthcare.

"What is an Automated External Defibrillator," American Heart Association, 2017 American Heart Association, retrieved at https://www.heart.org/-/media/data-import/downloadables/pe-abh-what-is-an-automated-external-defibrillator-ucm_300340.pdf on Jun. 20, 2019.

* cited by examiner

SMART AUTOMATED EXTERNAL DEFIBRILLATOR

BACKGROUND

According to the American Heart Association, 475,000 Americans die each year from cardiac arrest. Cardiac arrest is also a major cause of death globally, with cardiac arrest killing more people than colorectal cancer, breast cancer, prostate cancer, pneumonia, auto accidents, human immunodeficiency virus ("HIV"), firearms, and house fires combined. Cardiopulmonary resuscitation ("CPR") and automated external defibrillators ("AEDs") are the two main life saving measures used on victims of cardiac arrest.

An AED is a device administered to a victim of cardiac arrest in an attempt to stop the victim's irregular heartbeat (known as an arrhythmia) and cause the heart to resume normal rhythm. If cardiac arrest is not treated within minutes, the victim will die. The majority of cardiac arrest victims experience ventricular fibrillation ("VF"), which is a rapid and unsynchronized heart rhythm that originates in the ventricles of the heart. VF requires the heart to be defibrillated as soon as possible, since the victim's chance of survival drops 7-10% for each minute their heart beats irregularly.

SUMMARY

Concepts and technologies disclosed herein are directed to a smart automated external defibrillator ("AED"). According to one aspect of the concepts and technologies disclosed herein, the AED can present, on a display, a menu that includes a plurality of modes. The plurality of modes can include a first responder mode, an Internet of Things ("IoT") mode, and a general use mode. The AED can receive, via an input component, a selection, from the menu, of a mode from the plurality of modes. In response to the selection, the AED can configure a network connectivity component in accordance with a setting specified in the mode.

The first responder mode, when selected, can configure the network connectivity component to connect to a dedicated public safety network. The IoT mode, when selected, can configure the network connectivity component to enter a low power mode during which the network connectivity component periodically reports a battery status of a battery to an entity responsible for the AED. The general use mode, when selected, can configure the network connectivity component to connect to an emergency service via a network. The emergency service allows a user of the AED to access a set of advanced functions protected by a credential.

In some embodiments, in the IoT mode, the AED can determine if the battery status is below a threshold. In response to determining the battery status is below the threshold, the AED can reduce its functionality to a set of core functions, and can request, from the entity, maintenance to restore the battery status of the battery to the entity.

It should be appreciated that the above-described subject matter may be implemented as a computer-controlled apparatus, a computer process, a computing system, or as an article of manufacture such as a computer-readable storage medium. These and various other features will be apparent from a reading of the following Detailed Description and a review of the associated drawings.

This Summary is provided to introduce a selection of concepts in a simplified form that are further described below in the Detailed Description. This Summary is not intended to identify key features or essential features of the claimed subject matter, nor is it intended that this Summary be used to limit the scope of the claimed subject matter. Furthermore, the claimed subject matter is not limited to implementations that solve any or all disadvantages noted in any part of this disclosure.

DETAILED DESCRIPTION

While the subject matter described herein may be presented, at times, in the general context of program modules that execute in conjunction with the execution of an operating system and application programs on a computer system, those skilled in the art will recognize that other implementations may be performed in combination with other types of program modules. Generally, program modules include routines, programs, components, data structures, computer-executable instructions, and/or other types of structures that perform particular tasks or implement particular abstract data types. Moreover, those skilled in the art will appreciate that the subject matter described herein may be practiced with other computer systems, including hand-held devices, mobile devices, wireless devices, multiprocessor systems, distributed computing systems, microprocessor-based or programmable consumer electronics, minicomputers, mainframe computers, routers, switches, other computing devices described herein, and the like.

Figure 1:
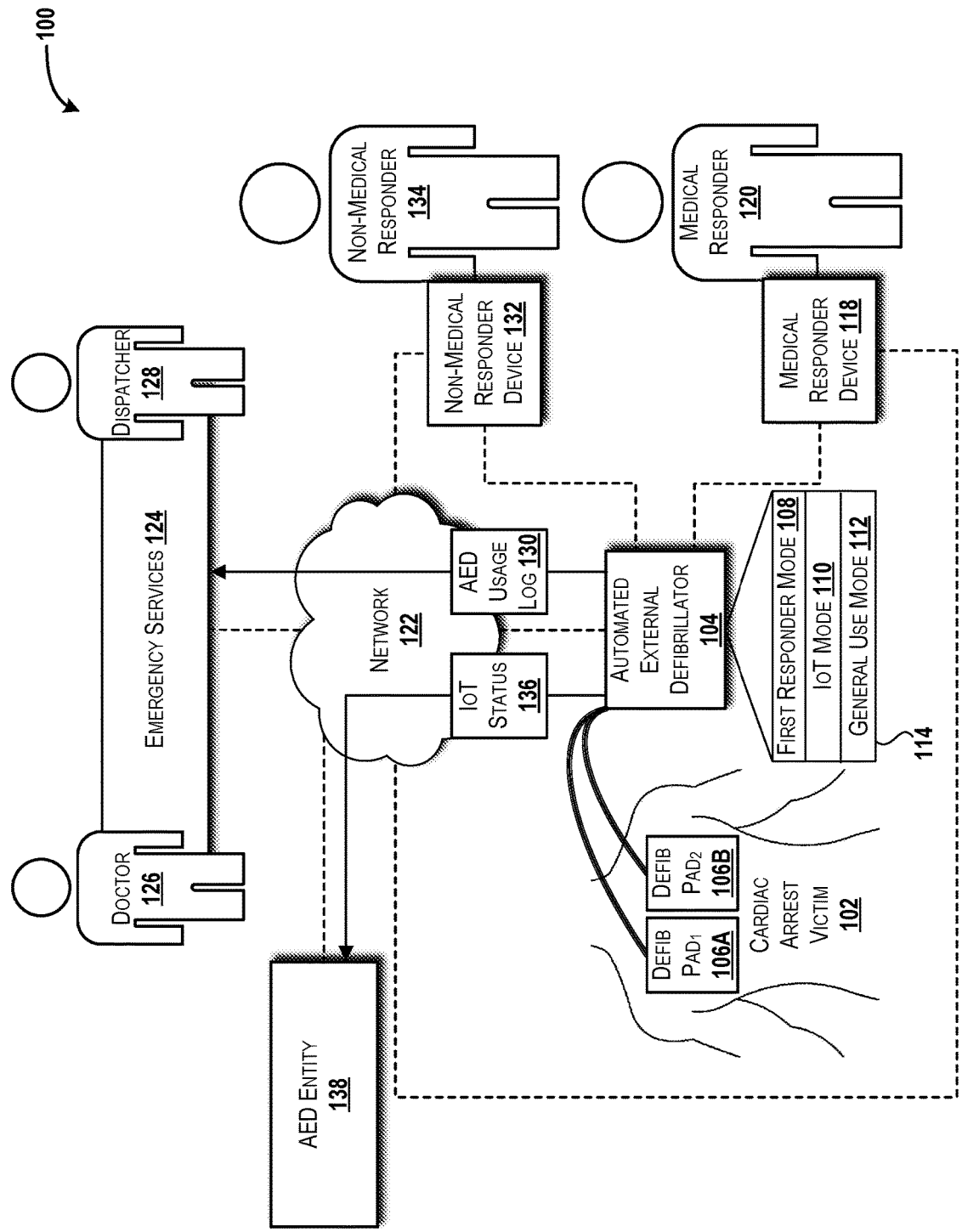
FIG. 1 is a block diagram illustrating an exemplary operating environment in which aspects of the concepts and technologies disclosed herein can be implemented.

Turning now to FIG. 1, an operating environment 100 in which aspects of the concepts and technologies disclosed herein can be implemented will be described. The operating environment 100 depicts a cardiac arrest victim 102 who is being treated, at least in part, via an automated external defibrillator ("AED") 104. In particular, the AED 104 is connected to defibrillator pads 106A, 106B that are used to provide an electric shock to the cardiac arrest victim 102 in an attempt to return the heart of the cardiac arrest victim 102 to a normal working state. The general concepts of cardiac arrest and the use of defibrillation devices to restore proper heart rhythm are well-known, and therefore, additional explanation of these concepts is not provided herein in favor of a focus on the new functionality provided by the AED 104.

The AED 104 can operate in a plurality of modes, including a first responder mode 108, an IoT mode 110, and a general use mode 112. The modes 108-112 can be presented by the AED 104 in a menu 114. The menu 114 can be a visual menu presented, for example, on a display of the AED 104 (best shown in FIG. 2). The menu additionally or alternatively can be an audio menu presented, for example, via a speaker of the AED 104 (also best shown in FIG. 2). The AED 104 can present the menu 114 via one or more other devices, such as a non-medical responder device 132 or a medical responder device 118 that is in communication with the AED 104, and in other ways not specifically described herein.

The first responder mode 108 enables a first responder function set of the AED 104. The first responder mode 108 can be selected by a medical responder 120, such as an emergency medical technician ("EMT"), paramedic, fireman, policeman, or any other personnel authorized to access the first responder mode 108. Access to the first responder mode 108 can be protected via one or more credentials. The credentials can include any identifier, password, code, biometric (e.g., fingerprint recognition, face recognition, voice recognition, retina recognition, combinations thereof, and the like), or other credential that instructs the AED 104 to allow the medical responder 120 access to the first responder function set of the AED 104. The credentials can be provided by the medical responder 120 via manual entry (e.g., credentials entered via an input component of the AED 104), via biometric scan, via swiping an ID card (e.g., wherein credentials are encoded in a magnetic strip on the ID card), or other interaction directly via the AED 104. Alternatively, the credentials can be entered on another device, such as the medical responder device 118, and provided via near-field communications ("NFC"), BLUETOOTH, or other connection to the AED 104.

The first responder function set can include priority access to a network 122. In some embodiments, the network 122 is or includes a dedicated public safety network, such as a First Responder Network Authority ("FirstNet") network, that provides first responders with exclusive access to certain radio spectrum. The first responder function set can enable communications to one or more emergency services 124, which can offer additional resources to the medical responder 120, such as resources provided, at least in part, by one or more doctors 126 and/or one or more dispatchers 128 (e.g., 9-1-1 dispatcher(s)). Nurses and other medical professionals, including other first responders also are contemplated. Moreover, the emergency services 124 can provide automated instructions to the medical responder 120 as an alternative to or in addition to any instructions provided locally by the AED 104.

The AED 104 can record interactions between the medical responder 120 and the AED 104 in an AED usage log 130. The AED 104 can provide the AED usage log 130 to the emergency services 124. In this manner, the doctor(s) 126, the dispatcher(s) 128, other individuals, hospitals, ambulances, systems, devices, and the like that are associated with the emergency services 124 can be notified of how the AED 104 was used by the medical responder 120 in treating the cardiac arrest victim 102.

The AED 104 may not have access to the network 122 due to a lack of network access capabilities of the AED 104, congestion, other issues with the network 122, and/or for other reasons. In such scenarios, the AED 104 can be tethered to the medical responder device 118, which can provide the AED 104 access to the network 122. Moreover, in some instances, the medical responder device 118 may be at least partially disabled or otherwise unavailable for tethering; in which case, the AED 104 can be tethered to another device in the vicinity of the cardiac arrest victim 102, such as a non-medical responder device 132 associated with a non-medical responder 134. In other instances, a first responder, such as the medical responder 120, may not be immediately available (e.g., en route), and since time is of the essence for the cardiac arrest victim 102, the medical responder 120 can remotely access the AED 104 to provide his/her credentials to select the first responder mode 108, and thereby enable the first responder function set for use by the non-medical responder 134 at the instruction of the medical responder 120.

The IoT mode 110 can enable a reliable, low power mode for day-to-day management of the AED 104. The IoT mode 110 enables the AED 104 to periodically report an IoT status 136 to an AED entity 138 that is responsible for the AED 104. Responsibility for the AED 104 can include initial deployment of the AED 104, maintenance of the AED 104, updates/upgrades of the AED 104, and other tasks to ensure the AED 104 is always ready to be used. The IoT status 136 can include a battery status of a battery (best shown in FIG. 2) of the AED 104. The IoT status 136 can include a log, such as the AED usage log 130. The IoT status 136 can include other information with regard to the status of the AED 104 and/or one or more components of the AED 104, such as, for example, a certification status of the AED 104, a calibration status of the AED 104, a software and/or firmware version of the AED 104, and the like. In this manner, the IoT status 136 can be used to notify the AED entity 138 when the AED 104 needs maintenance, such as replacement of the battery, re-certification, re-calibration, and/or software/firmware update.

The general use mode 112 can be established as the default mode of the AED 104 in which the AED 104 has full broadband access inclusive of two-way guided voice communication with the doctor 126, the dispatcher 128, and/or other individual(s) associated with the emergency services 124. The AED 104 can provide real-time telemetry to the emergency services 124 in order to better direct the non-medical responder 134 in assisting the cardiac arrest victim 102 using the AED 104. Alternatively, the emergency services 124 can provide policy-based automated guidance if the dispatcher 128 or other medical professional is unavailable via the emergency services 124. In some embodiments, the emergency services 124 leverage, at least in part, a cloud-based policy engine to drive this automated guidance. Similarly, the non-medical responder 134 can communicate with the medical responder 120, such as when the medical responder 120 is en route. The general use mode 112 can provide support for other medical diagnostic and/or treatment functions, such as blood sampling, sweat sampling, saliva sampling, drug administration, blood pressure testing, oxygen saturation sampling, combinations thereof, and the like.

It should be understood that the first responder mode 108, the IoT mode 110, and the general use mode 112 are provided herein as exemplary examples of the AED 104 disclosed herein that can support multiple modes. In some embodiments, the AED 104 has a different number of modes. In any case, each mode of the AED 104 can include any number of settings that effect any functionality of the AED 104. In general, the first responder mode 108 described herein enables the AED 104 with a function set suitable for a first responder, such as the medical responder 120, to assist the cardiac arrest victim 102; the IoT mode 110 is intended to preserve battery life to extend the useable in-field use of the AED 104 before maintenance is required; and the general use mode 112 is intended to provide a function set suitable for a layperson, such as the non-medical responder 134, to assist the cardiac arrest victim 102, but also offers the ability to communicate with the dispatcher 128, the doctor 126, and/or the medical responder 120 to unlock more advanced functions that could be useful in saving the life of the cardiac arrest victim 102.

Figure 2:
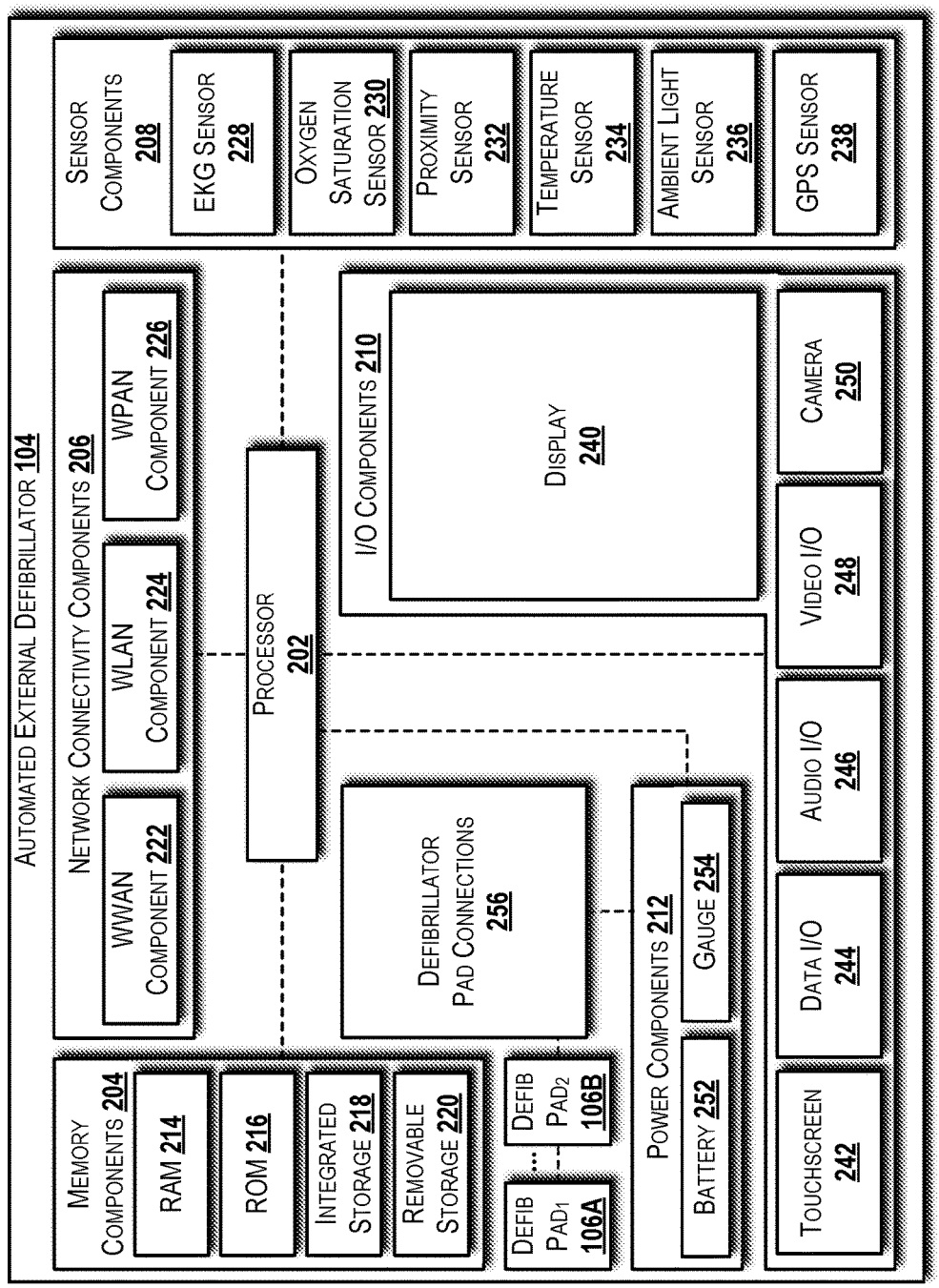
FIG. 2 is a block diagram illustrating an example automated external defibrillator and components thereof capable of implementing aspects of the embodiments presented herein.

Turning now to FIG. 2, an illustrative architecture 200 for the AED 104 will be described. In some embodiments, the AED 104 uses a variation of the architecture 200. As such, the illustrated embodiment of the architecture 200 of the AED 104 should not be construed as being limiting in any way. The architecture 200 illustrated in FIG. 2 includes a processor 202, memory components 204, network connectivity components 206, sensor components 208, input/output components 210, and power components 212, each of which will be described in detail below.

In the illustrated embodiment, the processor 202 is in communication with the memory components 204, the network connectivity components 206, the sensor components 208, the input/output ("I/O") components 210, and the power components 212. Although no connections are shown between the individual components illustrated in FIG. 2, the components can interact to carry out device functions. In some embodiments, the components are arranged so as to communicate via one or more busses (not shown).

The processor 202 can include a central processing unit ("CPU") configured to process data, execute computer-executable instructions of one or more application programs, and communicate with other components of the architecture 200 in order to perform various functions described herein. The processor 202 may be utilized to execute aspects of the software components presented herein.

In some embodiments, the processor 202 includes a graphics processing unit ("GPU") configured to accelerate operations performed by the CPU, including, but not limited to, operations performed by executing general-purpose scientific and/or engineering computing applications, as well as graphics-intensive computing applications such as high resolution video (e.g., 720P, 1080P, and higher resolution), three-dimensional ("3D") modeling applications, and the like. In some embodiments, the processor 202 is configured to communicate with a discrete GPU (not shown). In any case, the CPU and GPU may be configured in accordance with a co-processing CPU/GPU computing model, wherein the sequential part of an application executes on the CPU and the computationally-intensive part is accelerated by the GPU.

In some embodiments, the processor 202 is or is included in a system-on-chip ("SoC") along with one or more of the other components described below. For example, the SoC may include the processor 202, a GPU, one or more of the network connectivity components 206, and one or more of the sensor components 208. In some embodiments, the processor 202 is fabricated, at least in part, utilizing a package-on-package ("PoP") integrated circuit packaging technique. The processor 202 may be a single core or multi-core processor.

The processor 202 may be created in accordance with an ARM architecture, available for license from ARM HOLDINGS of Cambridge, United Kingdom. Alternatively, the processor 202 may be created in accordance with an x86 architecture, such as is available from INTEL CORPORATION of Mountain View, Calif. and others. In some embodiments, the processor 202 is a SNAPDRAGON SoC, available from QUALCOMM of San Diego, Calif.; a TEGRA SoC, available from NVIDIA of Santa Clara, Calif.; a HUMMINGBIRD SoC, available from SAMSUNG of Seoul, South Korea; an Open Multimedia Application Platform ("OMAP") SoC, available from TEXAS INSTRUMENTS of Dallas, Tex.; a customized version of any of the above SoCs; or a proprietary SoC.

The memory components 204 include a RAM 214, a read-only memory ("ROM") 216, an integrated storage memory ("integrated storage") 218, and a removable storage memory ("removable storage") 220. In some embodiments, the RAM 214 or a portion thereof, the ROM 216 or a portion thereof, and/or some combination the RAM 214 and the ROM 216 is integrated with the processor 202. In some embodiments, the ROM 216 is configured to store a firmware, an operating system or a portion thereof (e.g., operating system kernel), and/or a bootloader to load an operating system kernel from the integrated storage 218 and/or the removable storage 220.

The integrated storage 218 can include a solid-state memory, a hard disk, or a combination of solid-state memory and a hard disk. The integrated storage 218 may be soldered or otherwise connected to a logic board upon which the processor 202 and other components described herein also may be connected. As such, the integrated storage 218 is integrated in the AED 104. The integrated storage 218 is configured to store an operating system or portions thereof, application programs, data, and other software components described herein.

The removable storage 220 can include a solid-state memory, a hard disk, or a combination of solid-state memory and a hard disk. In some embodiments, the removable storage 220 is provided in lieu of the integrated storage 218. In other embodiments, the removable storage 220 is provided as additional optional storage. In some embodiments, the removable storage 220 is logically combined with the integrated storage 218 such that the total available storage is made available as a total combined storage capacity. In some embodiments, the total combined capacity of the integrated storage 218 and the removable storage 220 is shown to a user instead of separate storage capacities for the integrated storage 218 and the removable storage 220.

The removable storage 220 is configured to be inserted into a removable storage memory slot (not shown) or other mechanism by which the removable storage 220 is inserted and secured to facilitate a connection over which the removable storage 220 can communicate with other components of the AED 104, such as the processor 202. The removable storage 220 may be embodied in various memory card formats, including, but not limited to, PC card, CompactFlash card, memory stick, secure digital ("SD"), miniSD, microSD, universal integrated circuit card ("UICC") (e.g., a subscriber identity module ("SIM") or universal SIM ("USIM")), a proprietary format, or the like. The removable storage 220 is configured to store an operating system or portions thereof, application programs, data, and other software components described herein.

It should be understood that one or more of the memory components 204 can store an operating system for the AED 104. According to various embodiments, the operating system can include, but is not limited to, SYMBIAN OS from SYMBIAN LIMITED; WINDOWS mobile OS from Microsoft Corporation of Redmond, Wash.; WINDOWS phone OS from Microsoft Corporation; WINDOWS from Microsoft Corporation; PALM WEBOS from Hewlett-Packard Company of Palo Alto, Calif.; BLACKBERRY OS from Research In Motion Limited of Waterloo, Ontario, Canada; IOS from Apple Inc. of Cupertino, Calif.; and ANDROID OS from Google Inc. of Mountain View, Calif. Other operating systems are contemplated.

The network connectivity components 206 can include a wireless wide area network ("WWAN") component 222, a wireless local area network ("WLAN") component 224, and a wireless personal area network ("WPAN") component 226. The network connectivity components 206 facilitate communications to and from networks, such as the network 122 and/or one or more other networks, which may be WWANs, WLANs, WPANs, or some combination thereof. Although only the network 122 is noted, the network connectivity components 206 may facilitate simultaneous communications with multiple networks. For example, the network connectivity components 206 may facilitate simultaneous communications with multiple networks via one or more of the WWAN components 222, one or more of the WLAN components 224, and/or one or more of the WPAN components 226.

In some embodiments, the WWAN component 222 is configured to provide dual-mode or multi-mode connectivity to the network 122 and/or one or more other networks. For example, the WWAN component 222 may be configured to provide connectivity to the network 122, wherein the network 122 provides service via Global System for Mobile communications ("GSM"), Universal Mobile Telecommunications System ("UMTS"), and Long-Term Evolution ("LTE") technologies, or via some other combination of existing or future mobile communications technologies. Alternatively, multiple WWAN components 222 may be utilized to perform such functionality, and/or provide additional functionality to support other non-compatible technologies (i.e., incapable of being supported by a single WWAN component). The WWAN component 222 may facilitate similar connectivity to multiple networks (e.g., a UMTS network and an LTE network).

The sensor components 208 include an echocardiogram ("ECG/EKG") sensor 228, an oxygen saturation sensor 230, a proximity sensor 232, a temperature sensor 234, an ambient light sensor 236, and a Global Positioning System sensor ("GPS sensor") 238. It is contemplated that other sensors, such as, but not limited to, other medical sensors, a shock detection sensor, a magnetometer, an accelerometer, and the like also may be incorporated in the architecture 200.

The EKG sensor 228 is configured to measure the electrical activity of the heartbeat of the cardiac arrest victim 102. The oxygen saturation sensor 230 is configured to measure the oxygen saturation in the blood of the cardiac arrest victim 102. The temperature sensor 234 is configured to measure the body temperature of the cardiac arrest victim 102. The AED 104 can support additional medical device sensors to measure other aspects of the health of the cardiac arrest victim. As such, the number and type of sensors that can be implemented within or otherwise utilized by the AED 104 should not be construed as being limiting in any way.

The proximity sensor 232 is configured to detect the presence of a person, such as the non-medical responder or the medical responder, in proximity to the AED 104 without direct contact. In some embodiments, the proximity sensor 232 detects the presence of a person's body and provides this information to an application program stored within one of the memory components 204 that utilizes the proximity information to enable or disable some functionality of the AED 104. For example, the AED 104 may turn on, change modes (e.g., from the IoT mode 108 to the first responder mode 108 or the general use mode 112), or perform some other action, such as turn on a display 240. Other uses of proximity as detected by the proximity sensor 232 are contemplated.

The ambient light sensor 236 is configured to measure ambient light. In some embodiments, the ambient light sensor 236 provides measurements to an application program stored within one of the memory components 204 in order to automatically adjust the brightness of the display 240 (described below) to compensate for low-light and high-light environments. Other uses of measurements obtained by the ambient light sensor 236 are contemplated.

The GPS sensor 238 is configured to receive signals from GPS satellites for use in calculating a location. The location calculated by the GPS sensor 238 may be used by any application program that requires or benefits from location information. For example, the location calculated by the GPS sensor 238 may be used with a navigation application program executed by the non-medical responder device 132 and/or the medical responder device 118 to provide directions from a location of the non-medical responder device 132 and/or the medical responder device 118 to a location of the AED 104. Moreover, the GPS sensor 238 may be used to provide location information to an external location-based service, such as one of the emergency services 124, for use by the dispatcher 128 in providing guidance to the medical responder 120 so that the medical responder 120 can find the location of the AED 104. The GPS sensor 238 may obtain location information generated via WI-FI, WIMAX, and/or cellular triangulation techniques utilizing one or more of the network connectivity components 206 to aid the GPS sensor 238 in obtaining a location fix. The GPS sensor 238 may also be used in assisted GPS ("A-GPS") systems.

The I/O components 210 include the display 240, a touchscreen 242, a data I/O interface component ("data I/O") 244, an audio I/O interface component ("audio I/O") 246, a video I/O interface component ("video I/O") 248, and a camera 250. In some embodiments, the display 240 and the touchscreen 242 are combined. In some embodiments, two or more of the data I/O component 244, the audio I/O component 246, and the video I/O component 248 are combined. The I/O components 210 may include discrete processors configured to support the various interfaces described below, or may include processing functionality built-in to the processor 202.

The display 240 is an output device configured to present information in a visual form. In particular, the display 240 may present the menu 114, graphical user interface ("GUI") elements, text, images, video, notifications, virtual buttons, virtual keyboards, messaging data, Internet content, device status, time, date, calendar data, preferences, map information, location information, and any other information that is capable of being presented in a visual form. In some embodiments, the display 240 is a liquid crystal display ("LCD") utilizing any active or passive matrix technology and any backlighting technology (if used). In some embodiments, the display 240 is an organic light emitting diode ("OLED") display. Other display types are contemplated.

The touchscreen 242 is an input device configured to detect the presence and location of a touch. The touchscreen 242 may be a resistive touchscreen, a capacitive touchscreen, a surface acoustic wave touchscreen, an infrared touchscreen, an optical imaging touchscreen, a dispersive signal touchscreen, an acoustic pulse recognition touchscreen, or may utilize any other touchscreen technology. In some embodiments, the touchscreen 242 is incorporated on top of the display 240 as a transparent layer to enable a user to use one or more touches to interact with objects or other information presented on the display 240. In other embodiments, the touchscreen 242 is a touch pad incorporated on a surface of the AED 104 that does not include the display 240. For example, the AED 104 may have the touchscreen 242 incorporated on top of the display 240 and a touch pad on another surface of the AED 104.

In some embodiments, the touchscreen 242 is a single-touch touchscreen. In other embodiments, the touchscreen 242 is a multi-touch touchscreen. In some embodiments, the touchscreen 242 is configured to detect discrete touches, single touch gestures, and/or multi-touch gestures. These are collectively referred to herein as gestures for convenience. Several gestures will now be described. It should be understood that these gestures are illustrative and are not intended to limit the scope of the appended claims. Moreover, the described gestures, additional gestures, and/or alternative gestures may be implemented in software for use with the touchscreen 242. As such, a developer may create gestures that are specific to a particular application program.

In some embodiments, the touchscreen 242 supports a tap gesture in which a user taps the touchscreen 242 once on an item (e.g., a virtual button representative of the first responder mode 108, the IoT mode 110, or the general use mode 112) presented on the display 240. The tap gesture may be used for various reasons including, but not limited to, opening, launching, waking up, or otherwise interacting with an application program or function thereof that is associated with the GUI element that the user taps. In some embodiments, the touchscreen 242 supports a double tap gesture in which a user taps the touchscreen 242 twice on to perform some function. The double tap gesture may be used for various reasons including, but not limited to, zooming in or zooming out in stages. In some embodiments, the touchscreen 242 supports a tap and hold gesture in which a user taps the touchscreen 242 and maintains contact for at least a pre-defined time. The tap and hold gesture may be used for various reasons including, but not limited to, opening a context-specific menu.

In some embodiments, the touchscreen 242 supports a pan gesture in which a user places a finger on the touchscreen 242 and maintains contact with the touchscreen 242 while moving the finger on the touchscreen 242. The pan gesture may be used for various reasons including, but not limited to, moving through screens, images, or menus at a controlled rate. Multiple finger pan gestures are also contemplated. In some embodiments, the touchscreen 242 supports a flick gesture in which a user swipes a finger in the direction the user wants the screen to move. The flick gesture may be used for various reasons including, but not limited to, scrolling horizontally or vertically through menus or pages. In some embodiments, the touchscreen 242 supports a pinch and stretch gesture in which a user makes a pinching motion with two fingers (e.g., thumb and forefinger) on the touchscreen 242 or moves the two fingers apart. The pinch and stretch gesture may be used for various reasons including, but not limited to, zooming gradually in or out of a website, map, graph, chart, or picture, for example.

Although the above gestures have been described with reference to the use one or more fingers for performing the gestures, other appendages such as toes or objects such as styluses may be used to interact with the touchscreen 242. As such, the above gestures should be understood as being illustrative, and should not be construed as being limiting in any way.

The data I/O interface component 244 is configured to facilitate input of data (e.g., via a keyboard, keypad, or other input device) to the AED 104 and output of data from the AED 104. In some embodiments, the data I/O interface component 244 includes a connector configured to provide wired connectivity between the AED 104 and a computer system or device such as the non-medical responder device 132 and/or the medical responder device 118. The connector may be a proprietary connector or a standardized connector such as universal serial bus ("USB"), micro-USB, mini-USB, or the like. In some embodiments, the connector is a dock connector for docking the non-medical responder device 132 or the medical responder device 118 to the AED 104, and/or the AED 104 with another device such as a docking station.

The audio I/O interface component 246 is configured to provide audio input and/or output capabilities to the AED 104. In some embodiments, the audio I/O interface component 246 includes a microphone configured to collect audio signals. In some embodiments, the audio I/O interface component 246 includes a headphone jack configured to provide connectivity for headphones or other external speakers. In some embodiments, the audio I/O interface component 246 includes a speaker for the output of audio signals. In some embodiments, the audio I/O interface component 246 includes an optical audio cable out. The audio I/O interface component 246 can be used by the medical responder 120 and/or the non-medical responder 134 to discuss with the doctor 126, the dispatcher 128, and/or others associated with the emergency services 124.

The video I/O interface component 248 is configured to provide video input and/or output capabilities to the AED 104. In some embodiments, the video I/O interface component 248 includes a video connector configured to receive video as input from another device such as the non-medical responder device 132 and/or the medical responder device 118, and to send video as output to another device such as the non-medical responder device 132 and/or the medical responder device 118. In some embodiments, the video I/O interface component 248 includes a High-Definition Multimedia Interface ("HDMI"), mini-HDMI, micro-HDMI, DisplayPort, or proprietary connector to input/output video content. In some embodiments, the video I/O interface component 248 or portions thereof is combined with the audio I/O interface component 246 or portions thereof. The video I/O interface component 248 can be used by the medical responder 120 and/or the non-medical responder 134 to share video images captured by the camera 250 with the doctor 126, the dispatcher 128, and/or others associated with the emergency services 124.

The camera 250 can be configured to capture still images and/or video. The camera 250 may utilize a charge coupled device ("CCD") or a complementary metal oxide semiconductor ("CMOS") image sensor to capture images. In some embodiments, the camera 250 includes a flash to aid in taking pictures in low-light environments. Settings for the camera 250 may be implemented as hardware or software buttons.

Although not illustrated, one or more hardware buttons may also be included in the architecture 200. The hardware buttons may be used for controlling some operational aspect of the AED 104 such as powering on/off, resetting the AED 104, setting or changing a mode of the AED 104, initiating defibrillation, and/or otherwise interacting with the AED 104. The hardware buttons may be dedicated buttons or multi-use buttons. The hardware buttons may be mechanical or sensor-based.

The illustrated power components 212 include one or more batteries 252, which can be connected to a battery gauge 254. The batteries 252 may be rechargeable or disposable. Rechargeable battery types include, but are not limited to, lithium polymer, lithium ion, nickel cadmium, and nickel metal hydride. Each of the batteries 252 may be made of one or more cells.

The battery gauge 254 can be configured to measure battery parameters such as current, voltage, and temperature.

In some embodiments, the battery gauge 254 is configured to measure the effect of a battery's discharge rate, temperature, age and other factors to predict remaining life within a certain percentage of error. In some embodiments, the battery gauge 254 provides measurements to an application program that is configured to utilize the measurements to present useful power management data to a user. Power management data may include one or more of a percentage of battery used, a percentage of battery remaining, a battery condition, a remaining time, a remaining capacity (e.g., in watt hours), a current draw, and a voltage. The battery gauge 254 can be used, for example, in the IoT mode 110, to report the battery status to the AED entity 138 via the IoT status 136.

The power components 212 may also include a power connector, which may be combined with one or more of the aforementioned I/O components 210. The power components 212 may interface with an external power system or charging equipment via a power I/O component (not shown). The power components 212 also may interface with one or more defibrillator pad connections 256 that provide power from the power components 212 to the defibrillator pads 106A-106B.

Turning now to FIGS. 3A-3D, aspects of a method 300 for providing a multi-mode AED will be described, according to an illustrative embodiment. It should be understood that the operations of the methods disclosed herein are not necessarily presented in any particular order and that performance of some or all of the operations in an alternative order(s) is possible and is contemplated. The operations have been presented in the demonstrated order for ease of description and illustration. Operations may be added, omitted, and/or performed simultaneously, without departing from the scope of the concepts and technologies disclosed herein.

It also should be understood that the illustrated methods can be ended at any time and need not be performed in their entirety. Some or all operations of the methods, and/or substantially equivalent operations, can be performed by execution of computer-executable instructions included on a computer-readable storage media, as defined below. The term "computer-executable instructions," and variants thereof, as used in the description and claims, is used expansively herein to include routines, application programs, software, application modules, program modules, components, data structures, algorithms, and the like. Computer-executable instructions can be implemented on various system configurations, including single-processor or multi-processor systems, distributed computing systems, mini-computers, mainframe computers, personal computers, hand-held computing devices, microprocessor-based, programmable consumer electronics, network nodes, combinations thereof, and the like.

Thus, it should be appreciated that the logical operations described herein may be implemented (1) as a sequence of computer implemented acts or program modules running on a computing system and/or (2) as interconnected machine logic circuits or circuit modules within the computing system. The implementation is a matter of choice dependent on the performance and other requirements of the computing system. Accordingly, the logical operations described herein are referred to variously as states, operations, structural devices, acts, or modules. These operations, structural devices, acts, and modules may be implemented in software, in firmware, in special purpose digital logic, and any combination thereof.

The method 300 begins and proceeds to operation 302, where the AED presents the menu 114 that includes the first responder mode 108, the IoT mode 110, and the general use mode 112. The menu 114 can be a visual menu presented, for example, on the display 240 of the AED 104. The menu additionally or alternatively can be an audio menu presented, for example, via the audio I/O 246 (e.g., a speaker) of the AED 104. The AED 104 can present the menu 114 via one or more other devices, such as a non-medical responder device 132 or a medical responder device 118 that is in communication with the AED 104, and in other ways not specifically described herein. From operation 302, the method 300 proceeds to operation 304, where the AED 104 receives a selection of a mode from the menu 114. From operation 304, the method 300 proceeds to operation 306, where the AED 104 determines which mode was selected.

In some embodiments, the AED 104 automatically switches to the IoT mode 110. The AED 104 may automatically switch to the IoT mode 110 after a specific amount of time has elapsed after the AED 104 was last used. Alternatively, the AED 104 may automatically switch to the IoT mode 110 periodically, based upon a schedule, or in response to another trigger. The AED 104 may automatically switch to other modes, such as the first responder mode 108 or the general use mode 112.

Figure 3A:
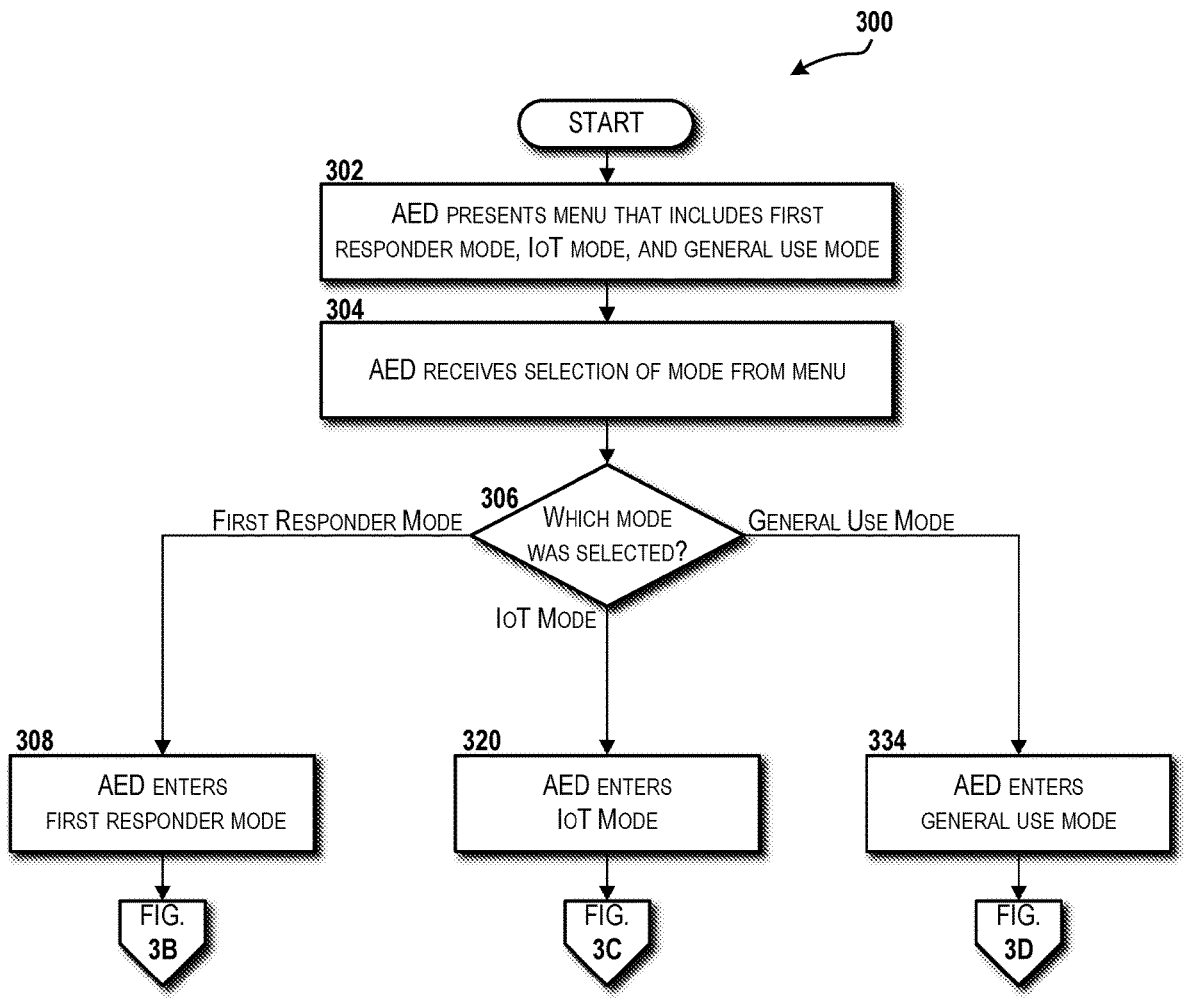
FIGS. 3A-3D illustrate a flow diagram of a method for providing a multi-mode automated external defibrillator, according to an illustrative embodiment.
Figure 3B:
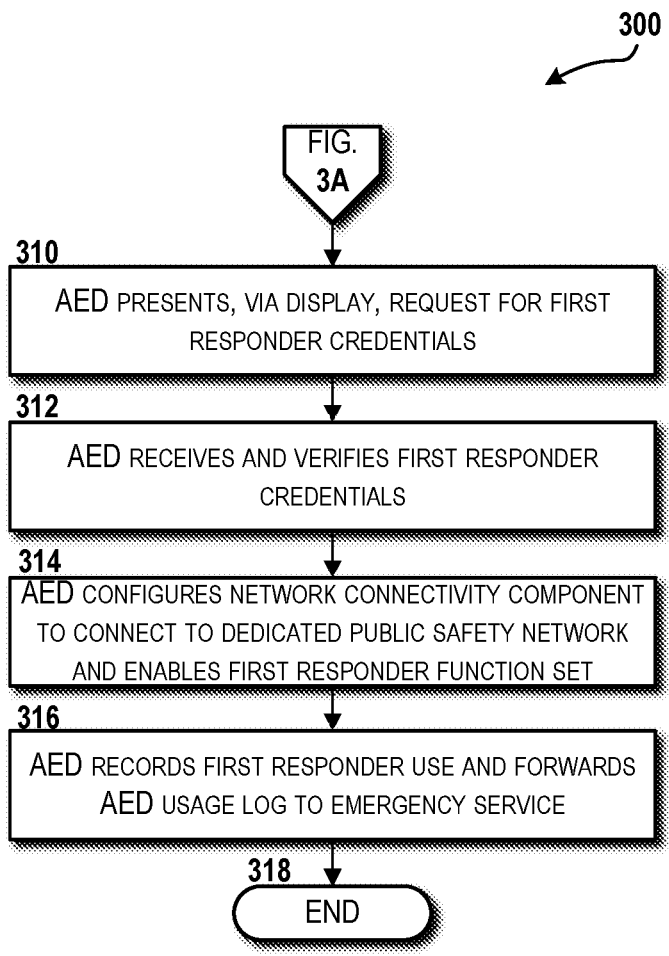

In response to the AED 104 determining that the first responder mode 108 was selected, the method proceeds to operation 308, where the AED 104 enters the first responder mode 108. From operation 308, the method 300 proceeds to operation 310, which is shown in FIG. 3B, where the AED 104 presents a request for first responder credentials. The request can be a text-based, picture-based, video-based, or audio-based request. The intention of the request is to prompt a first responder, such as the medical responder 120, to quickly provide his/her credentials. From operation 310, the method 300 proceeds to operation 312, where the AED 104 receives and verifies the first responder credentials, such as by communicating with the emergency services 124 and/or the AED entity 138 for verification. From operation 312, the method 300 proceeds to operation 314, where the AED 104 configures the network connectivity component 206 to connect to a dedicated public safety network and enables a first responder function set. From operation 314, the method 300 proceeds to operation 316, where the AED 104 records first responder use and forwards the AED usage log 130 to the emergency service(s) 124. From operation 316, the method 300 proceeds to operation 318, where the method 300 ends.

Figure 3C:
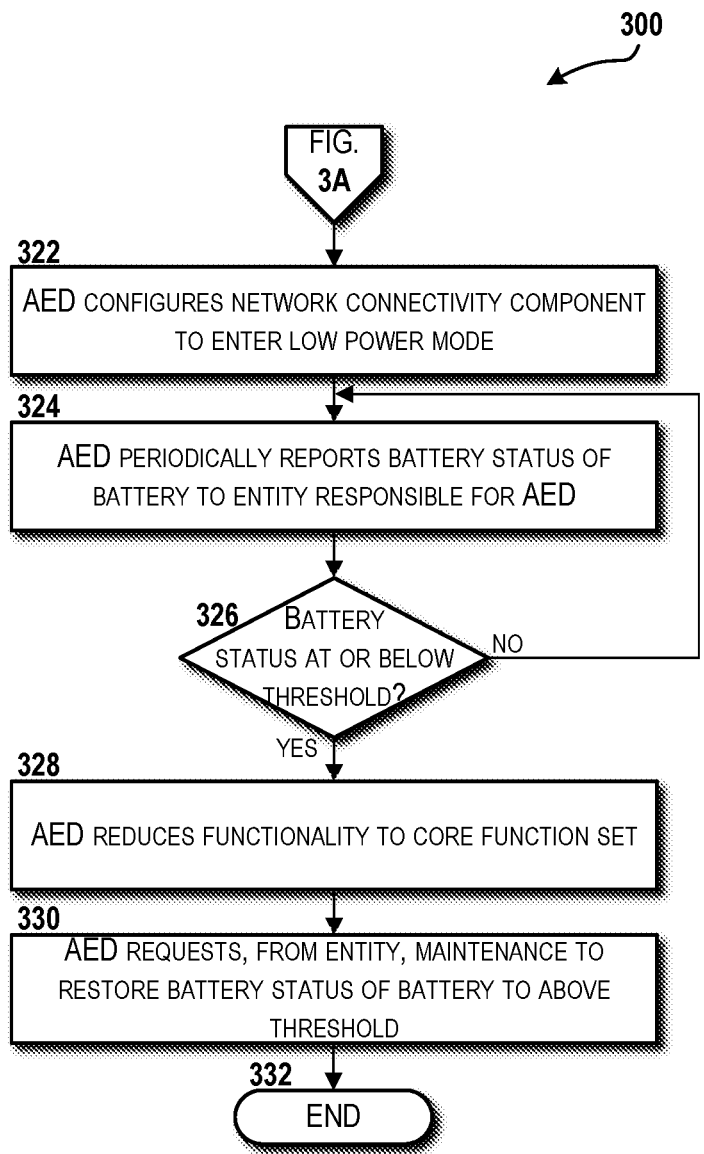

Returning to FIG. 3A, in response to the AED 104 determining that the IoT mode 110 was selected, the method proceeds to operation 320, where the AED 104 enters the IoT mode 110. From operation 320, the method 300 proceeds to operation 322, which is shown in FIG. 3C, where the AED 104 configures the network connectivity component 206 to enter a low power mode. From operation 322, the method 300 proceeds to operation 324, where the AED 104 periodically reports the battery status (e.g., as part of the IoT status 136) of the battery 252 to the AED entity 138 responsible for the AED 104. From operation 324, the method 300 proceeds to operation 326, where the AED 104 determines if the battery status is at or below a threshold. If the AED 104 determines the battery status is above the threshold, the method 300 returns to operation 324 and the method 300 proceeds as described above. If the AED 104 determines the battery status is at or below the threshold, the method 300 proceeds to operation 328, where the AED 104 reduces functionality to a core function set. The core function set can ensure the AED 104 remains in functional condition to administer a pre-determined number of defibrillation cycles in an effort to maximize battery life and thus availability of the AED 104 for someone in need, such as the cardiac arrest victim 102. From operation 328, the method 300 proceeds to operation 330, where the AED 104 requests, from the AED entity 138, maintenance to restore the battery status of the battery 252 to above the threshold. For example, the AED entity 138 may send a technician to the location of the AED 104 to repair, recharge, or replace the battery 252. The IoT status 136 can be used to inform the AED entity 138 of other issues with the AED 104. From operation 330, the method 300 proceeds to operation 332, where the method 300 ends.

As described above, the IoT status 136 can include information alternative to or in addition to the battery status. For example, the IoT status 136 can include a certification status of the AED 104, a calibration status of the AED 104, a software and/or firmware version of the AED 104, and the like. In this manner, the IoT status 136 can be used to notify the AED entity 138 when the AED 104 needs maintenance, such as replacement of the battery, re-certification, re-calibration, and/or software/firmware update.

Figure 3D:
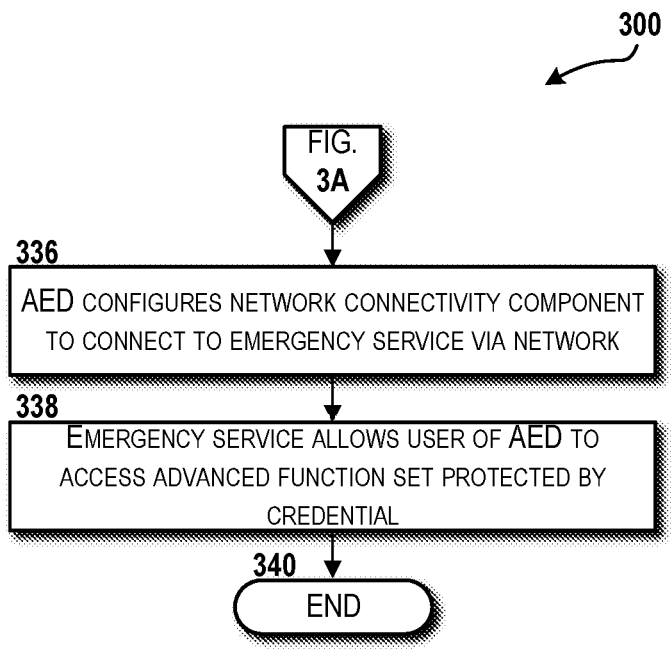

Returning to FIG. 3A, in response to the AED 104 determining that the general use mode 112 was selected, the method 300 proceeds to operation 334, where the AED 104 enters the general use mode 112. From operation 334, the method 300 proceeds to operation 336, which is shown in FIG. 3D, where the AED 104 configures the network connectivity component 206 to connect to the emergency service 124 via the network 122. From operation 336, the method 300 proceeds to operation 338, where the emergency service 124 allows a user of the AED 104 (e.g., the non-medical responder 134) to access an advanced function set protected by a credential. In particular, in addition to functionality of existing AEDs, including guided voice instructions, for example, the general use mode 112 can enable the non-medical responder 134 to conduct additional tests (e.g., via the sensor components 208), and/or otherwise have access to at least a portion of the functions provided in the first responder mode 108, at the discretion of the doctor 126, the dispatcher 128, and/or the medical responder 120. From operation 338, the method 300 proceeds to operation 340, where the method 300 ends.

Figure 4:
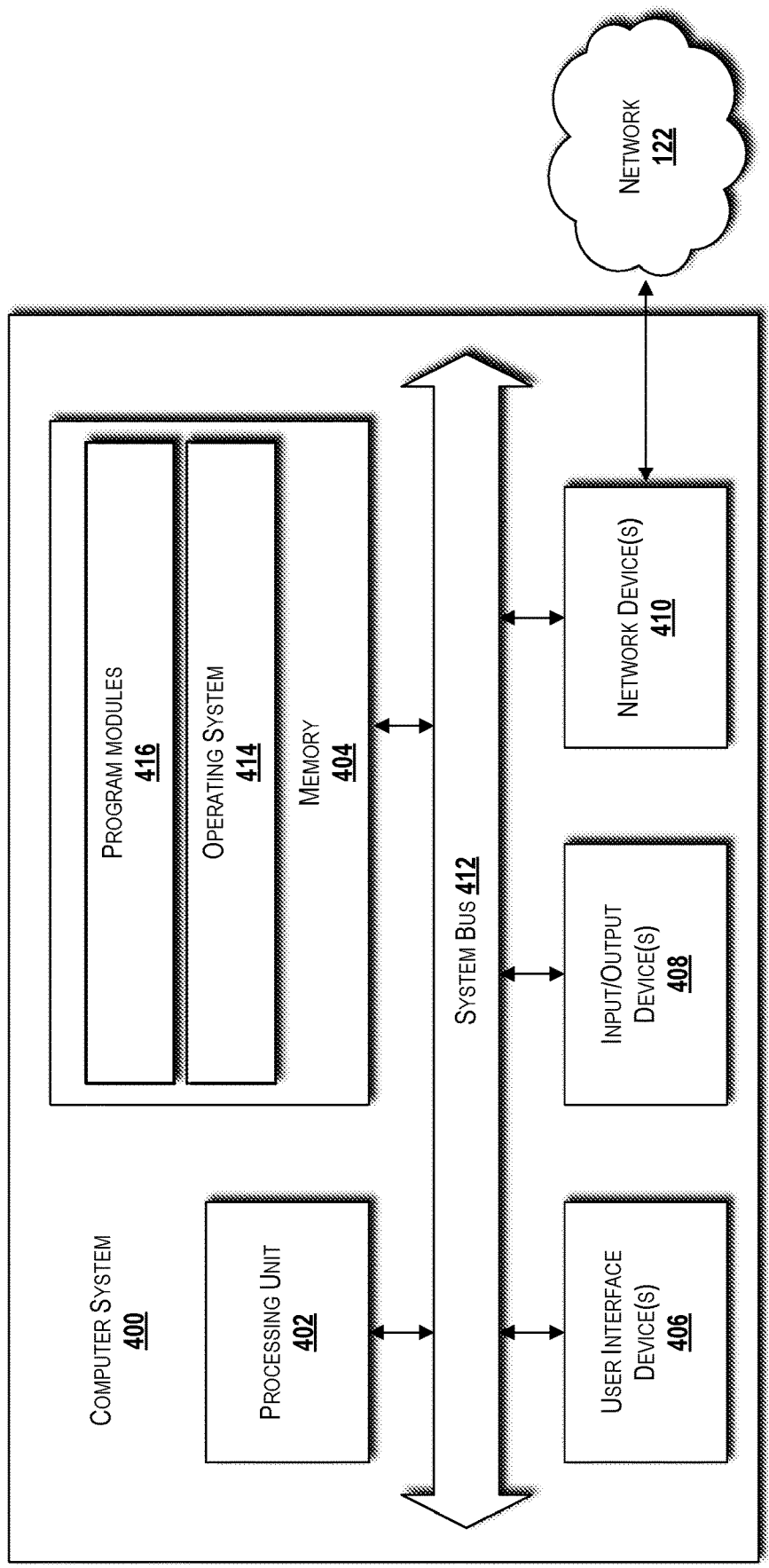
FIG. 4 is a block diagram illustrating an example computer system capable of implementing aspects of the embodiments presented herein.

Turning now to FIG. 4, a block diagram illustrating a computer system 400 configured to provide the functionality in accordance with various embodiments of the concepts and technologies disclosed herein. The non-medical responder device 132, the medical responder device 118, one or more systems and/or devices associated with the emergency services 124, other disclosed herein, or any combination thereof, can utilize or can execute upon, at least in part, an architecture that is the same as or at least similar to the architecture of the computer system 400. It should be understood, however, that modification to the architecture may be made to facilitate certain interactions among elements described herein.

The computer system 400 includes a processing unit 402, a memory 404, one or more user interface devices 406, one or more input/output ("I/O") devices 408, and one or more network devices 410, each of which is operatively connected to a system bus 412. The bus 412 enables bi-directional communication between the processing unit 402, the memory 404, the user interface devices 406, the I/O devices 408, and the network devices 410.

The processing unit 402 may be a standard central processor that performs arithmetic and logical operations, a more specific purpose programmable logic controller ("PLC"), a programmable gate array, or other type of processor known to those skilled in the art and suitable for controlling the operation of the server computer. Processing units are generally known, and therefore are not described in further detail herein.

The memory 404 communicates with the processing unit 402 via the system bus 412. In some embodiments, the memory 404 is operatively connected to a memory controller (not shown) that enables communication with the processing unit 402 via the system bus 412. The illustrated memory 404 includes an operating system 414 and one or more program modules 416. The operating system 414 can include, but is not limited to, members of the WINDOWS, WINDOWS CE, and/or WINDOWS MOBILE families of operating systems from MICROSOFT CORPORATION, the LINUX family of operating systems, the SYMBIAN family of operating systems from SYMBIAN LIMITED, the BREW family of operating systems from QUALCOMM CORPORATION, the MAC OS, OS X, and/or iOS families of operating systems from APPLE CORPORATION, the FREEBSD family of operating systems, the SOLARIS family of operating systems from ORACLE CORPORATION, other operating systems, and the like.

The program modules 416 may include various software and/or program modules to perform the various operations described herein. The program modules 416 and/or other programs can be embodied in computer-readable media containing instructions that, when executed by the processing unit 402, perform various operations such as those described herein. According to embodiments, the program modules 416 may be embodied in hardware, software, firmware, or any combination thereof.

By way of example, and not limitation, computer-readable media may include any available computer storage media or communication media that can be accessed by the computer system 400. Communication media includes computer-readable instructions, data structures, program modules, or other data in a modulated data signal such as a carrier wave or other transport mechanism and includes any delivery media. The term "modulated data signal" means a signal that has one or more of its characteristics changed or set in a manner as to encode information in the signal. By way of example, and not limitation, communication media includes wired media such as a wired network or direct-wired connection, and wireless media such as acoustic, RF, infrared and other wireless media. Combinations of the any of the above should also be included within the scope of computer-readable media.

Computer storage media includes volatile and non-volatile, removable and non-removable media implemented in any method or technology for storage of information such as computer-readable instructions, data structures, program modules, or other data. Computer storage media includes, but is not limited to, RAM, ROM, Erasable Programmable ROM ("EPROM"), Electrically Erasable Programmable ROM ("EEPROM"), flash memory or other solid state memory technology, CD-ROM, digital versatile disks ("DVD"), or other optical storage, magnetic cassettes, magnetic tape, magnetic disk storage or other magnetic storage devices, or any other medium which can be used to store the desired information and which can be accessed by the computer system 400. In the claims, the phrase "computer storage medium" and variations thereof does not include waves or signals per se and/or communication media.

The user interface devices 406 may include one or more devices with which a user accesses the computer system 400. The user interface devices 406 may include, but are not limited to, computers, servers, PDAs, cellular phones, or any suitable computing devices. The I/O devices 408 enable a user to interface with the program modules 416. In one embodiment, the I/O devices 408 are operatively connected to an I/O controller (not shown) that enables communication with the processing unit 402 via the system bus 412. The I/O devices 408 may include one or more input devices, such as, but not limited to, a keyboard, a mouse, or an electronic stylus. Further, the I/O devices 408 may include one or more output devices, such as, but not limited to, a display screen or a printer. In some embodiments, the I/O devices 408 can be used for manual controls for operations to exercise under certain emergency situations.

The network devices 410 enable the computer system 400 to communicate with other networks or remote systems via the network 122. Examples of the network devices 410 include, but are not limited to, a modem, a RF or infrared ("IR") transceiver, a telephonic interface, a bridge, a router, or a network card. The network 418 may be or may include a wireless network such as, but not limited to, a WLAN, a WWAN, a WPAN such as provided via BLUETOOTH technology, a Wireless Metropolitan Area Network ("WMAN") such as a WiMAX network or metropolitan cellular network.

Figure 5:
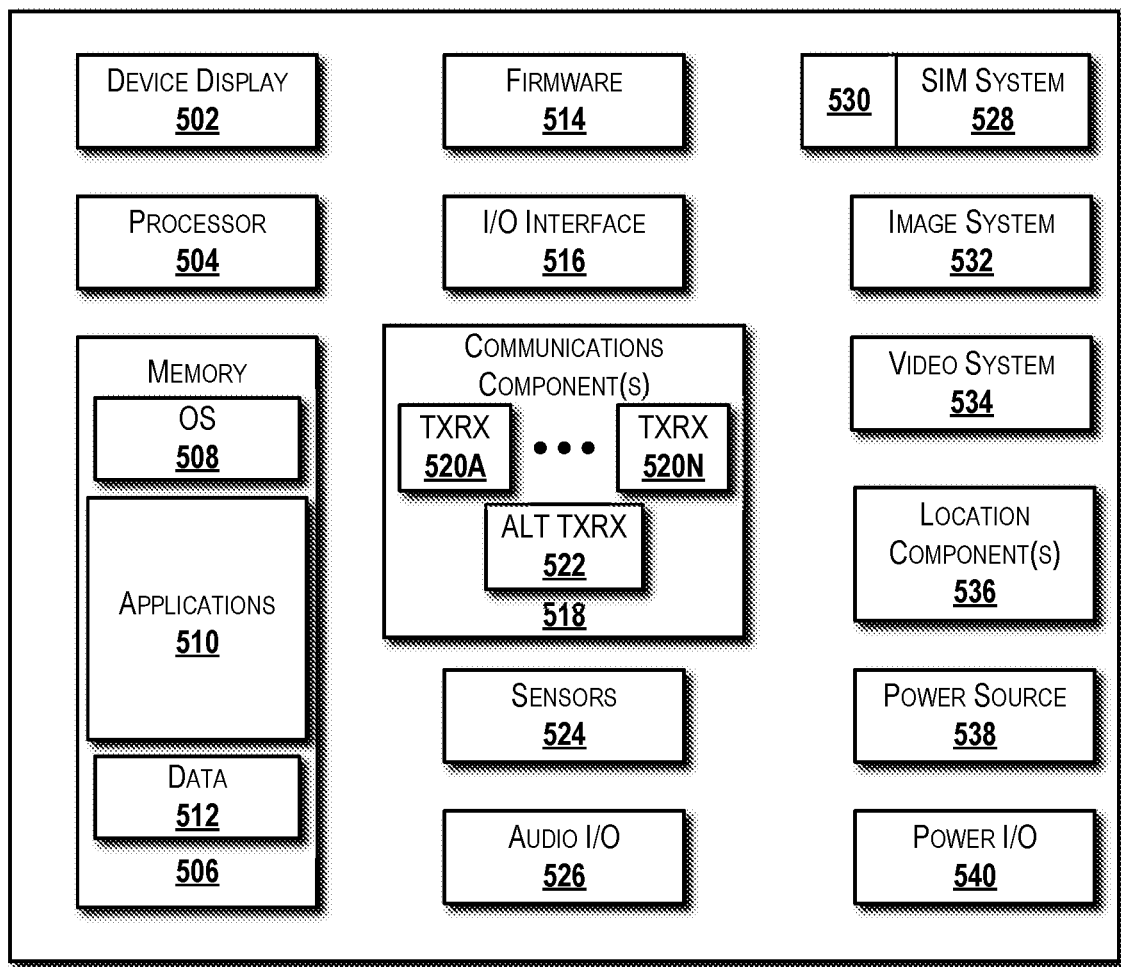
FIG. 5 is a block diagram illustrating an example mobile device capable of implementing aspects of the embodiments disclosed herein.

Turning now to FIG. 5, a block diagram illustrating an example mobile device 500, according to an illustrative embodiment. The non-medical responder device 132, the medical responder device 118, one or more devices associated with the emergency services 124, other disclosed herein, or any combination thereof, can utilize or can execute upon, at least in part, an architecture that is the same as or at least similar to the architecture of the computer system 400.

While connections are not shown between the various components illustrated in FIG. 5, it should be understood that some, none, or all of the components illustrated in FIG. 5 can be configured to interact with one other to carry out various device functions. In some embodiments, the components are arranged so as to communicate via one or more busses (not shown). Thus, it should be understood that FIG. 5 and the following description are intended to provide a general understanding of a suitable environment in which various aspects of embodiments can be implemented, and should not be construed as being limiting in any way.

As illustrated in FIG. 5, the mobile device 500 can include a device display 502 for displaying data. According to various embodiments, the device display 502 can be configured to display various graphical user interface ("GUI") elements, text, images, video, virtual keypads and/or keyboards, messaging data, notification messages, metadata, internet content, device status, time, date, calendar data, device preferences, map and location data, combinations thereof, and/or the like. The mobile device 500 also can include a processor 504 and a memory or other data storage device ("memory") 506. The processor 504 can be configured to process data and/or can execute computer-executable instructions stored in the memory 506. The computer-executable instructions executed by the processor 504 can include, for example, an operating system 508, one or more applications 510, other computer-executable instructions stored in a memory 506, or the like. In some embodiments, the applications 510 also can include a user interface ("UP") application (not illustrated in FIG. 5).

The UI application can interface with the operating system 508 to facilitate user interaction with functionality and/or data stored at the mobile device 500 and/or stored elsewhere. In some embodiments, the operating system 508 can include a member of the SYMBIAN OS family of operating systems from SYMBIAN LIMITED, a member of the WINDOWS MOBILE OS and/or WINDOWS PHONE OS families of operating systems from MICROSOFT CORPORATION, a member of the PALM WEBOS family of operating systems from HEWLETT PACKARD CORPORATION, a member of the BLACKBERRY OS family of operating systems from RESEARCH IN MOTION LIMITED, a member of the IOS family of operating systems from APPLE INC., a member of the ANDROID OS family of operating systems from GOOGLE INC., and/or other operating systems. These operating systems are merely illustrative of some contemplated operating systems that may be used in accordance with various embodiments of the concepts and technologies described herein and therefore should not be construed as being limiting in any way.

The UI application can be executed by the processor 504 to aid a user in entering content, viewing account information, answering/initiating calls, entering/deleting data, entering and setting user IDs and passwords for device access, configuring settings, manipulating address book content and/or settings, multimode interaction, interacting with other applications 510, and otherwise facilitating user interaction with the operating system 508, the applications 510, and/or other types or instances of data 512 that can be stored at the mobile device 500. The data 512 can include, for example, one or more identifiers, and/or other applications or program modules. According to various embodiments, the data 512 can include, for example, medical data associated with the cardiac arrest victim 102, credentials for the medical responder 120, credentials for the non-medical responder 134, and other data associated with providing assistance to the cardiac arrest victim 102, including medical records of the cardiac arrest victim 102, emergency contact information, and the like. The applications 510 can include one or more applications to support video calls with the doctor 126 and/or the dispatcher 128, one or more applications to support voice calls with the doctor 126 and/or the dispatcher 128, other medical applications, presence applications, messaging applications, text-to-speech and speech-to-text applications, add-ons, plug-ins, email applications, camera applications, location-based service applications, power conservation applications, productivity applications, enterprise applications, combinations thereof, and the like. The applications 510, the data 512, and/or portions thereof can be stored in the memory 506 and/or in a firmware 514, and can be executed by the processor 504. The firmware 514 also can store code for execution during device power up and power down operations. It can be appreciated that the firmware 514 can be stored in a volatile or non-volatile data storage device including, but not limited to, the memory 506 and/or a portion thereof.

The mobile device 500 also can include an input/output ("I/O") interface 516. The I/O interface 516 can be configured to support the input/output of data such as medical data, credentials, location information, organization information, presence status information, user IDs, passwords, and application initiation (start-up) requests. In some embodiments, the I/O interface 516 can include a hardwire connection such as USB port, a mini-USB port, a micro-USB port, an audio jack, a PS2 port, an IEEE 1394 ("FIREWIRE") port, a serial port, a parallel port, an Ethernet (RJ45) port, an RJ10 port, a proprietary port, combinations thereof, or the like. In some embodiments, the mobile device 500 can be configured to synchronize with another device, such as the AED 104, to transfer content to and/or from the mobile device 500. In some embodiments, the mobile device 500 can be configured to receive updates to one or more of the applications 510 via the I/O interface 516, though this is not necessarily the case. In some embodiments, the I/O interface 516 accepts I/O devices such as keyboards, keypads, mice, interface tethers, printers, plotters, external storage, touch/multi-touch screens, touch pads, trackballs, joysticks, microphones, remote control devices, displays, projectors, medical equipment (e.g., stethoscopes, heart monitors, and other health metric monitors), modems, routers, external power sources, docking stations, combinations thereof, and the like. It should be appreciated that the I/O interface 516 may be used for communications between the mobile device 500 and a network device or local device.

The mobile device 500 also can include a communications component 518. The communications component 518 can be configured to interface with the processor 504 to facilitate wired and/or wireless communications with one or more networks such as one or more IP access networks and/or one or more circuit access networks. In some embodiments, other networks include networks that utilize non-cellular wireless technologies such as WI-FI or WIMAX. In some embodiments, the communications component 518 includes a multimode communications subsystem for facilitating communications via the cellular network and one or more other networks.

The communications component 518, in some embodiments, includes one or more transceivers. The one or more transceivers, if included, can be configured to communicate over the same and/or different wireless technology standards with respect to one another. For example, in some embodiments one or more of the transceivers of the communications component 518 may be configured to communicate using GSM, code division multiple access ("CDMA") ONE, CDMA2000, LTE, and various other 2G, 2.5G, 3G, 4G, 5G, and greater generation technology standards. Moreover, the communications component 518 may facilitate communications over various channel access methods (which may or may not be used by the aforementioned standards) including, but not limited to, time-division multiple access ("TDMA"), frequency-division multiple access ("FDMA"), wideband CDMA ("W-CDMA"), orthogonal frequency-division multiplexing ("OFDM"), space-division multiple access ("SDMA"), and the like.

In addition, the communications component 518 may facilitate data communications General Packet Radio Service ("GPRS"), Enhanced Data rates for Global Evolution ("EDGE"), the High-Speed Packet Access ("HSPA") protocol family including High-Speed Downlink Packet Access ("HSDPA"), Enhanced UpLink ("EUL") or otherwise termed High-Speed Uplink Packet Access ("HSUPA"), HSPA+, and various other current and future wireless data access standards. In the illustrated embodiment, the communications component 518 can include a first transceiver ("TxRx") 520A that can operate in a first communications mode (e.g., GSM). The communications component 518 also can include an N$^{th}$ transceiver ("TxRx") 520N that can operate in a second communications mode relative to the first transceiver 520A (e.g., UMTS). While two transceivers 520A-520N (hereinafter collectively and/or generically referred to as "transceivers 520") are shown in FIG. 5, it should be appreciated that less than two, two, and/or more than two transceivers 520 can be included in the communications component 518.

The communications component 518 also can include an alternative transceiver ("Alt TxRx") 522 for supporting other types and/or standards of communications. According to various contemplated embodiments, the alternative transceiver 522 can communicate using various communications technologies such as, for example, WI-FI, WIMAX, BLUETOOTH, infrared, infrared data association ("IRDA"), near-field communications ("NFC"), ZIGBEE, other radio frequency ("RF") technologies, combinations thereof, and the like.

In some embodiments, the communications component 518 also can facilitate reception from terrestrial radio networks, digital satellite radio networks, internet-based radio service networks, combinations thereof, and the like. The communications component 518 can process data from a network such as the Internet, an intranet, a broadband network, a WI-FI hotspot, an Internet service provider ("ISP"), a digital subscriber line ("DSL") provider, a broadband provider, combinations thereof, or the like.

The mobile device 500 also can include one or more sensors 524. The sensors 524 can include medical sensors (e.g., EKG/ECG sensors, oxygen saturation sensors, and/or the like), temperature sensors, light sensors, air quality sensors, movement sensors, orientation sensors, noise sensors, proximity sensors, or the like. As such, it should be understood that the sensors 524 can include, but are not limited to, accelerometers, magnetometers, gyroscopes, infrared sensors, noise sensors, microphones, combinations thereof, or the like. Additionally, audio capabilities for the mobile device 500 may be provided by an audio I/O component 526. The audio I/O component 526 of the mobile device 500 can include one or more speakers for the output of audio signals, one or more microphones for the collection and/or input of audio signals, and/or other audio input and/or output devices.

The illustrated mobile device 500 also can include a subscriber identity module ("SIM") system 528. The SIM system 528 can include a universal SIM ("USIM"), a universal integrated circuit card ("UICC") and/or other identity devices. The SIM system 528 can include and/or can be connected to or inserted into an interface such as a slot interface 530. In some embodiments, the slot interface 530 can be configured to accept insertion of other identity cards or modules for accessing various types of networks. Additionally, or alternatively, the slot interface 530 can be configured to accept multiple subscriber identity cards. Because other devices and/or modules for identifying users and/or the mobile device 500 are contemplated, it should be understood that these embodiments are illustrative, and should not be construed as being limiting in any way.

The mobile device 500 also can include an image capture and processing system 532 ("image system"). The image system 532 can be configured to capture or otherwise obtain photos, videos, and/or other visual information. As such, the image system 532 can include cameras, lenses, charge-coupled devices ("CCDs"), combinations thereof, or the like. The mobile device 500 may also include a video system 534. The video system 534 can be configured to capture, process, record, modify, and/or store video content. Photos and videos obtained using the image system 532 and the video system 534, respectively, may be added as message content to an MMS message, email message, and sent to another mobile device. The video and/or photo content also can be shared with other devices via various types of data transfers via wired and/or wireless communication devices as described herein.

The mobile device 500 also can include one or more location components 535. The location components 536 can be configured to send and/or receive signals to determine a geographic location of the mobile device 500. According to various embodiments, the location components 536 can send and/or receive signals from GPS devices, assisted GPS ("A-GPS") devices, WI-FI/WIMAX and/or cellular network triangulation data, combinations thereof, and the like. The location component 536 also can be configured to communicate with the communications component 518 to retrieve triangulation data for determining a location of the mobile device 500. In some embodiments, the location component 536 can interface with cellular network nodes, telephone lines, satellites, location transmitters and/or beacons, wireless network transmitters and receivers, combinations thereof, and the like. In some embodiments, the location component 536 can include and/or can communicate with one or more of the sensors 524 such as a compass, an accelerometer, and/or a gyroscope to determine the orientation of the mobile device 500. Using the location component 536, the mobile device 500 can generate and/or receive data to identify its geographic location, or to transmit data used by other devices to determine the location of the mobile device 500. The location component 536 may include multiple components for determining the location and/or orientation of the mobile device 500.

The illustrated mobile device 500 also can include a power source 538. The power source 538 can include one or more batteries, power supplies, power cells, and/or other power subsystems including alternating current ("AC") and/or direct current ("DC") power devices. The power source 538 also can interface with an external power system or charging equipment via a power I/O component 540. Because the mobile device 500 can include additional and/or alternative components, the above embodiment should be understood as being illustrative of one possible operating environment for various embodiments of the concepts and technologies described herein. The described embodiment of the mobile device 500 is illustrative, and should not be construed as being limiting in any way.

Figure 6:
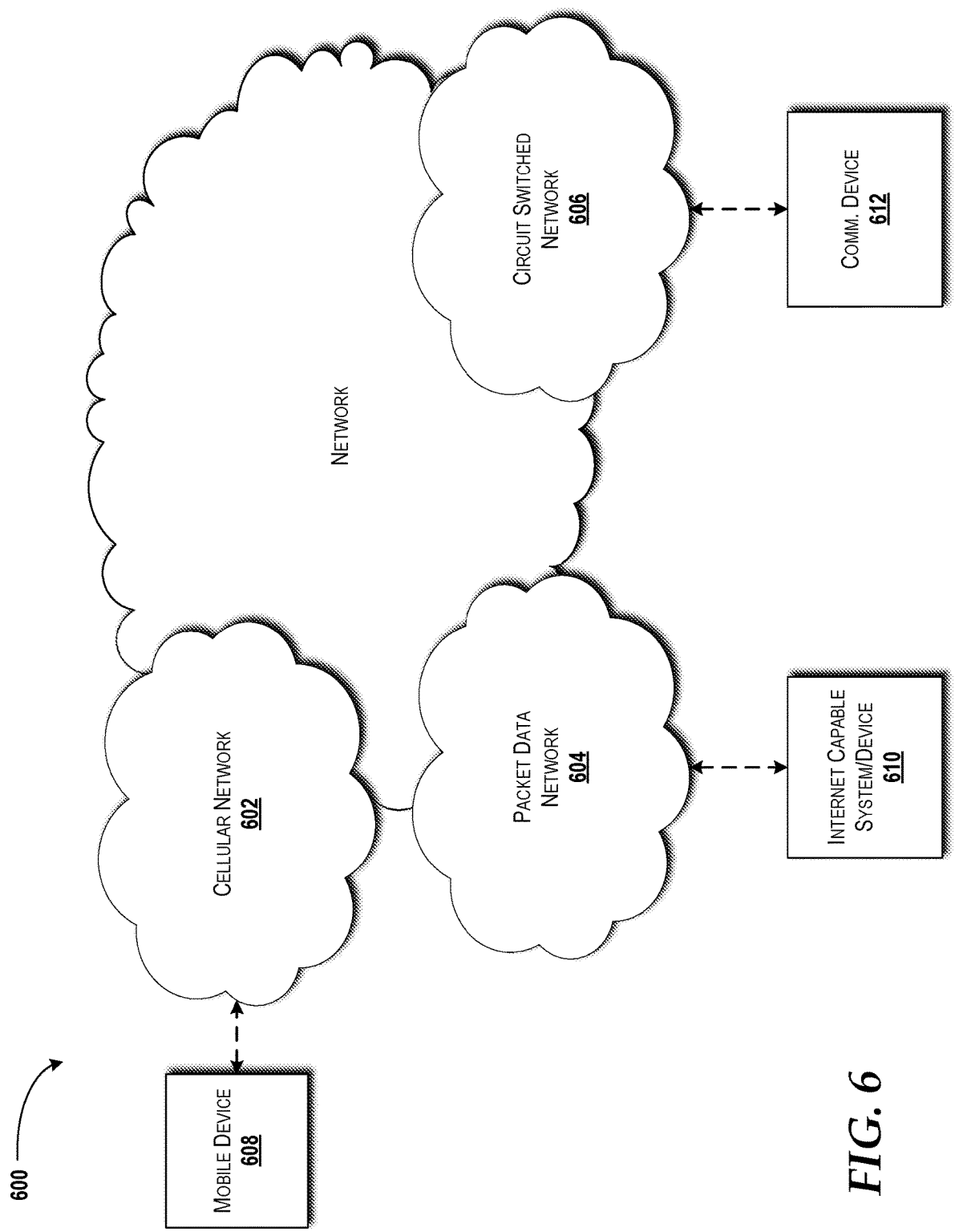
FIG. 6 is a block diagram schematically illustrating a network, according to an illustrative embodiment.

Turning now to FIG. 6, a schematic illustration of a network 600 will be described, according to an illustrative embodiment. In some embodiments, the network 122 is or includes the network 600 or some portion(s) thereof. The network 600 includes a cellular network 602, a packet data network 604, for example, the Internet, and a circuit switched network 606, for example, a publicly switched telephone network ("PSTN"). The cellular network 602 includes various components such as, but not limited to, base transceiver stations ("BTSs"), Node-B's or e-Node-B's, base station controllers ("BSCs"), radio network controllers ("RNCs"), mobile switching centers ("MSCs"), mobile management entities ("MMEs"), short message service centers ("SMSCs"), multimedia messaging service centers ("MMSCs"), home location registers ("HLRs"), home subscriber servers ("HSSs"), visitor location registers ("VLRs"), charging platforms, billing platforms, voicemail platforms, GPRS core network components, location service nodes, an IP Multimedia Subsystem ("IMS"), and the like. The cellular network 602 also includes radios and nodes for receiving and transmitting voice, data, and combinations thereof to and from radio transceivers, networks, the packet data network 604, and the circuit switched network 606.

A mobile communications device 612, such as, for example, the mobile device 500, the non-medical responder device 132, the medical responder device 118, a mobile terminal, a PDA, a laptop computer, a handheld computer, and combinations thereof, can be operatively connected to the cellular network 602. The cellular network 602 can be configured as a 2G GSM network and can provide data communications via GPRS and/or EDGE. Additionally, or alternatively, the cellular network 602 can be configured as a 3G UMTS network and can provide data communications via the HSPA protocol family, for example, HSDPA, EUL (also referred to as HSUPA), and HSPA+. The cellular network 602 also is compatible with 4G mobile communications standards as well as evolved and future mobile standards.

The packet data network 604 includes various devices, for example, the AED 104, the non-medical responder device 132, the medical responder device 118, servers, computers, databases, and other devices in communication with one another, as is generally known. The packet data network 604 devices are accessible via one or more network links. The servers often store various files that are provided to a requesting device such as, for example, a computer, a terminal, a smartphone, or the like. Typically, the requesting device includes software (a "browser") for executing a web page in a format readable by the browser or other software. Other files and/or data may be accessible via "links" in the retrieved files, as is generally known. In some embodiments, the packet data network 604 includes or is in communication with the Internet. The circuit switched network 606 includes various hardware and software for providing circuit switched communications. The circuit switched network 606 may include, or may be, what is often referred to as a plain old telephone system ("POTS"). The functionality of a circuit switched network 606 or other circuit-switched network are generally known and will not be described herein in detail.

The illustrated cellular network 602 is shown in communication with the packet data network 604 and a circuit switched network 606, though it should be appreciated that this is not necessarily the case. One or more Internet-capable devices 610, for example, the AED 104, the non-medical responder device 132, the medical responder device 118, a PC, a laptop, a portable device, or another suitable device, can communicate with one or more cellular networks 602, and devices connected thereto, through the packet data network 604. It also should be appreciated that the Internet-capable device 610 can communicate with the packet data network 604 through the circuit switched network 606, the cellular network 602, and/or via other networks (not illustrated).

As illustrated, a communications device 612, for example, a telephone, facsimile machine, modem, computer, or the like, can be in communication with the circuit switched network 606, and therethrough to the packet data network 604 and/or the cellular network 602. It should be appreciated that the communications device 612 can be an Internet-capable device, and can be substantially similar to the Internet-capable device 610. In the specification, the network 600 is used to refer broadly to any combination of the networks 602, 604, 606. It should be appreciated that substantially all of the functionality described with reference to the network 600 can be performed by the cellular network 602, the packet data network 604, and/or the circuit switched network 606, alone or in combination with other networks, network elements, and the like. The network 600 can include the functionality of any of the networks described herein.

Based on the foregoing, it should be appreciated that concepts and technologies directed to a smart AED have been disclosed herein. Although the subject matter presented herein has been described in language specific to computer structural features, methodological and transformative acts, specific computing machinery, and computer-readable media, it is to be understood that the concepts and technologies disclosed herein are not necessarily limited to the specific features, acts, or media described herein. Rather, the specific features, acts and mediums are disclosed as example forms of implementing the concepts and technologies disclosed herein.

The subject matter described above is provided by way of illustration only and should not be construed as limiting. Various modifications and changes may be made to the subject matter described herein without following the example embodiments and applications illustrated and described, and without departing from the true spirit and scope of the embodiments of the concepts and technologies disclosed herein.

The invention claimed is:

1. A method comprising:
presenting, on a display of an automated external defibrillator, a menu comprising a plurality of modes, wherein the plurality of modes comprise a first responder mode, an Internet of Things ("IoT") mode, and a general use mode;
receiving, via an input component of the automated external defibrillator, a selection, from the menu, of the first responder mode from the plurality of modes, wherein the first responder mode enables a first responder function set and wherein access to the first responder mode and the first responder function set is protected by a credential;
in response to receiving the selection of the first responder mode from the plurality of modes and the credential, configuring, by the automated external defibrillator, a network connectivity component of the automated external defibrillator to connect to a dedicated public safety network;
after an amount of time, automatically switching, by the automated external defibrillator, from the first responder mode to the IoT mode; and
while in the IoT mode,
providing, by the automated external defibrillator, an IoT status of the automated external defibrillator to an entity associated with the automated external defibrillator, wherein the IoT status comprises a battery status of a battery of the automated external defibrillator,
determining, by the automated external defibrillator, that the battery status of the battery of the automated external defibrillator is at or below a threshold,
in response to determining that the battery status is at or below the threshold,
reducing, by the automated external defibrillator, functionality of the automated external defibrillator to a set of core functions, wherein the set of core functions maintains the automated external defibrillator in a functional condition to administer a predetermined number of defibrillation cycles, and
requesting, by the automated external defibrillator, from the entity, maintenance to restore the battery status of the battery to above the threshold,
detecting, by a proximity sensor of the automated external defibrillator, a presence of a body without direct contact with the body,
in response to detecting the presence of a body, switching, by the automated external defibrillator, from the IoT mode to the general use mode; and
in response to switching to the general use mode, configuring the network connectivity component of the automated external defibrillator to connect to an emergency service via a network, wherein the emergency service allows a user of the automated external defibrillator to access, while in the general use mode, a set of advanced functions that comprise at least a portion of the first responder function set otherwise protected by the credential.

2. The method of claim 1, further comprising in response to switching to the IoT mode, configuring, by the automated external defibrillator, the network connectivity component of the automated external defibrillator to enter a low power mode.

3. The method of claim 1, wherein the IoT status further comprises at least one of a log of how the automated external defibrillator has been used, a certification status of the automated external defibrillator, a calibration status of the automated external defibrillator, or a software version of the automated external defibrillator.

4. The method of claim 1, further comprising receiving, via the input component of the automated external defibrillator, a selection, from the menu, of the IoT mode from the plurality of modes presented in the menu.

5. The method of claim 4, further comprising configuring the network connectivity component of the automated external defibrillator to enter a low power mode during which the network connectivity component periodically reports the battery status of the battery to the entity associated with the automated external defibrillator.

6. The method of claim 1, further comprising receiving, via the input component of the automated external defibrillator, a selection, from the menu, of the general use mode from the plurality of modes presented in the menu.

7. A computer-readable storage medium having instructions stored herein that, when executed by a processor of an automated external defibrillator, cause the processor to perform operations comprising:
presenting, on a display of the automated external defibrillator, a menu comprising a plurality of modes, wherein the plurality of modes comprise a first responder mode, an Internet of Things ("IoT") mode, and a general use mode;
receiving, via an input component of the automated external defibrillator, a selection, from the menu, of the first responder mode from the plurality of modes, wherein the first responder mode enables a first responder function set and wherein access to the first responder mode and the first responder function set is protected by a credential;
in response to receiving the selection of the first responder mode from the plurality of modes and the credential, configuring, a network connectivity component of the automated external defibrillator to connect to a dedicated public safety network;
after an amount of time, automatically switching from the first responder mode to the IoT mode; and
while in the IoT mode,
providing an IoT status of the automated external defibrillator to an entity associated with the automated external defibrillator, wherein the IoT status comprises a battery status of a battery of the automated external defibrillator,
determining that the battery status of the battery of the automated external defibrillator is at or below a threshold,
in response to determining that the battery status is at or below the threshold,
reducing functionality of the automated external defibrillator to a set of core functions, wherein the set of core functions maintains the automated external defibrillator in a functional condition to administer a predetermined number of defibrillation cycles, and requesting, from the entity, maintenance to restore the battery status of the battery to above the threshold, detecting, by a proximity sensor of the automated external defibrillator, a presence of a body without direct contact with the body, in response to detecting the presence of a body, switching from the IoT mode to the general use mode, and in response to switching to the general use mode, configuring the network connectivity component of the automated external defibrillator to connect to an emergency service via a network, wherein the emergency service allows a user of the automated external defibrillator to access, while in the general use mode, a set of advanced functions that comprise at least a portion of the first responder function set otherwise protected by the credential.

8. The computer-readable storage medium of claim 7, wherein the operations further comprise in response to switching to the IoT mode, configuring the network connectivity component of the automated external defibrillator to enter a low power mode.

9. The computer-readable storage medium of claim 7, wherein the IoT status further comprises at least one of a log of how the automated external defibrillator has been used, a certification status of the automated external defibrillator, a calibration status of the automated external defibrillator, or a software version of the automated external defibrillator.

10. The computer-readable storage medium of claim 7, wherein the operations further comprise receiving, via the input component of the automated external defibrillator, a selection, from the menu, of the IoT mode from the plurality of modes presented in the menu.

11. The computer-readable storage medium of claim 10, wherein the operations further comprise configuring the network connectivity component of the automated external defibrillator to enter a low power mode during which the network connectivity component periodically reports the battery status of the battery to the entity associated with the automated external defibrillator.

12. The computer-readable storage medium of claim 7, wherein the operations further comprise receiving, via the input component of the automated external defibrillator, a selection, from the menu, of the general use mode from the plurality of modes presented in the menu.

13. An automated external defibrillator comprising
a display;
an input component;
a network connectivity component;
a proximity sensor;
a processor; and
a memory comprising computer-executable instructions that, when executed by the processor, cause the processor to perform operations comprising
presenting, on the display, a menu comprising a plurality of modes, wherein the plurality of modes comprise a first responder mode, an Internet of Things ("IoT") mode, and a general use mode,
receiving, via the input component, a selection, from the menu, of the first responder mode from the plurality of modes, wherein the first responder mode enables a first responder function set and wherein access to the first responder mode and the first responder function set is protected by a credential,
in response to receiving the selection of the first responder mode from the plurality of modes and the credential, configuring the network connectivity component of the automated external defibrillator to connect to a dedicated public safety network,
after an amount of time, automatically switching from the first responder mode to the IoT mode, and
while in the IoT mode,
providing an IoT status of the automated external defibrillator to an entity associated with the automated external defibrillator, wherein the IoT status comprises a battery status of a battery of the automated external defibrillator,
determining that the battery status of the battery of the automated external defibrillator is at or below a threshold,
in response to determining that the battery status is at or below the threshold,
reducing functionality of the automated external defibrillator to a set of core functions, wherein the set of core functions maintains the automated external defibrillator in a functional condition to administer a predetermined number of defibrillation cycles, and
requesting, from the entity, maintenance to restore the battery status of the battery to above the threshold,
detecting, by the proximity sensor, a presence of a body without direct contact with the body,
in response to detecting the presence of a body, switching from the IoT mode to the general use mode, and
in response to switching to the general use mode, configuring the network connectivity component of the automated external defibrillator to connect to an emergency service via a network, wherein the emergency service allows a user of the automated external defibrillator to access, while in the general use mode, a set of advanced functions that comprise at least a portion of the first responder function set otherwise protected by the credential.

14. The automated external defibrillator of claim 13, wherein the operations further comprise in response to switching to the IoT mode, configuring the network connectivity component of the automated external defibrillator to enter a low power mode based on switching to the IoT mode.

15. The automated external defibrillator of claim 13, wherein the IoT status further comprises at least one of a log of how the automated external defibrillator has been used, a certification status of the automated external defibrillator, a calibration status of the automated external defibrillator, or a software version of the automated external defibrillator.

16. The automated external defibrillator of claim 13, wherein the operations further comprise receiving, via the input component, a selection, from the menu, of the general use mode from the plurality of modes presented in the menu.

* * * * *